United States Patent
Sasaki et al.

(10) Patent No.: US 10,888,364 B2
(45) Date of Patent: Jan. 12, 2021

(54) SCOOP CANNULA WITH DEFLECTABLE WINGS

(71) Applicant: Medtronic Holding Company Sàrl, Tolochenaz (CH)

(72) Inventors: Neil Sasaki, San Jose, CA (US); Hester Chan, Sunnyvale, CA (US); Mojan Goshayeshgar, Atherton, CA (US)

(73) Assignee: MEDTRONIC HOLDING COMPANY SARL, Tolochenaz (CH)

( * ) Notice: Subject to any disclaimer, the term of this patent is extended or adjusted under 35 U.S.C. 154(b) by 152 days.

(21) Appl. No.: 15/859,816

(22) Filed: Jan. 2, 2018

(65) Prior Publication Data

US 2019/0201066 A1 Jul. 4, 2019

(51) Int. Cl.
A61B 17/88 (2006.01)
A61B 17/00 (2006.01)

(52) U.S. Cl.
CPC ...... *A61B 17/8855* (2013.01); *A61B 17/8811* (2013.01); *A61B 17/8858* (2013.01); *A61B 17/8805* (2013.01); *A61B 2017/00867* (2013.01)

(58) Field of Classification Search
CPC .. A61B 17/88; A61B 17/8855; A61B 17/8811
See application file for complete search history.

(56) References Cited

U.S. PATENT DOCUMENTS

| | | | |
|---|---|---|---|
| 4,207,891 A | 6/1980 | Bolduc | |
| 4,630,616 A | 12/1986 | Tretinyak | |
| 4,795,446 A | 1/1989 | Fecht | |
| 4,838,282 A | 6/1989 | Strasser et al. | |
| 5,195,507 A * | 3/1993 | Bilweis | A61B 1/00082 600/204 |
| 5,262,296 A | 11/1993 | Ogawa et al. | |
| 5,295,980 A | 3/1994 | Ersek | |
| 5,385,151 A | 1/1995 | Scarfone et al. | |
| 5,501,654 A | 3/1996 | Failla et al. | |
| 5,531,722 A | 7/1996 | Van Hale | |
| 5,807,277 A | 9/1998 | Swaim | |
| 5,876,383 A | 3/1999 | Grooters et al. | |
| 6,186,967 B1 | 2/2001 | Grooters | |
| 6,447,525 B2 | 9/2002 | Follmer et al. | |
| 6,494,868 B2 | 12/2002 | Amar | |
| 6,575,919 B1 | 6/2003 | Reiley et al. | |
| 6,755,793 B2 | 6/2004 | Lamoureux et al. | |
| 6,875,183 B2 | 4/2005 | Cervi | |
| 6,949,108 B2 | 9/2005 | Holmes | |
| 6,979,318 B1 | 12/2005 | McDonald et al. | |

(Continued)

FOREIGN PATENT DOCUMENTS

| EP | 1703923 B1 | 9/2006 |
| EP | 1708621 A2 | 10/2006 |
| EP | 1748722 A2 | 2/2007 |

*Primary Examiner* — Christopher J Beccia
(74) *Attorney, Agent, or Firm* — Sorell, Lenna & Schmidt, LLP (57) ABSTRACT

A kyphoplasty cannula includes a shaft extending between opposite first and second end surfaces. The shaft includes an inner surface defining a lumen. The shaft includes a first opening that extends through the first end surface and a second opening that extends through the second end surface. A scoop extends from the second end surface. The scoop includes an arcuate surface that is continuous with the inner surface. Kits and methods of use are disclosed.

20 Claims, 8 Drawing Sheets

(56) References Cited

U.S. PATENT DOCUMENTS

| | | |
|---|---|---|
| 7,044,954 B2 | 5/2006 | Reiley et al. |
| 7,500,947 B2 | 3/2009 | Kucklick et al. |
| 7,510,549 B2 | 3/2009 | Rue et al. |
| 7,691,060 B2 | 4/2010 | Seward et al. |
| 7,708,713 B2 | 5/2010 | Albrecht et al. |
| 7,713,273 B2 | 5/2010 | Krueger et al. |
| 7,892,216 B2 | 2/2011 | Fangrow, Jr. |
| 7,938,794 B2 | 5/2011 | Rehman et al. |
| 8,052,641 B2 | 11/2011 | Hiejima et al. |
| 8,088,081 B2 | 1/2012 | Field et al. |
| 8,167,899 B2 | 5/2012 | Justis et al. |
| 8,251,950 B2 | 8/2012 | Albert et al. |
| 8,257,322 B2 | 9/2012 | Koehler et al. |
| 8,323,251 B2 | 12/2012 | West et al. |
| 8,702,743 B2 * | 4/2014 | Bierhoff ............... A61B 17/221 606/191 |
| 8,709,362 B2 * | 4/2014 | Leventhal ............... B01L 3/18 422/547 |
| 2005/0273076 A1 | 12/2005 | Beasley et al. |
| 2007/0010845 A1 | 1/2007 | Gong et al. |
| 2009/0216238 A1 | 8/2009 | Stark |
| 2010/0185116 A1 | 7/2010 | Al-Mohizea |
| 2010/0198140 A1 | 8/2010 | Lawson |
| 2010/0222745 A1 | 9/2010 | Burkholz |
| 2011/0202062 A1 | 8/2011 | O'Halloran et al. |
| 2011/0202065 A1 | 8/2011 | Takizawa et al. |
| 2012/0010624 A1 | 1/2012 | O'Halloran et al. |
| 2012/0143206 A1 | 6/2012 | Wallace et al. |
| 2012/0330241 A1 | 12/2012 | Haddock et al. |
| 2013/0013007 A1 * | 1/2013 | Broome ............ A61B 17/8822 606/86 R |
| 2014/0214085 A1 | 7/2014 | Druma |
| 2014/0235997 A1 * | 8/2014 | Smith ................ A61B 17/3472 600/424 |
| 2015/0127104 A1 * | 5/2015 | Levy .................... A61F 2/4612 623/14.12 |

* cited by examiner

SCOOP CANNULA WITH DEFLECTABLE WINGS

TECHNICAL FIELD

The present disclosure generally relates to surgical devices, and more particularly to a scoop cannula with deflectable wings configured for use in a kyphoplasty procedure. Kits and methods of use are disclosed.

BACKGROUND

Height loss is commonly associated with spinal fractures, such as, for example, vertebral compression fractures. Spinal fractures affect a large segment of osteoporotic patients. It is estimated that approximately 700,000 spinal fractures occur annually from osteoporosis, for example. Procedures have been developed to treat spinal fractures. One such procedure is kyphoplasty. Kyphoplasty is a minimally invasive procedure that is used to treat spinal fractures, such as, for example, vertebral compression fractures by inserting one or more balloons, such as, for example, compliant balloons inside a fractured vertebral body. The balloon or balloons are inflated within the fractured vertebral body such that the cancellous bone of the vertebral body is pushed towards cortical walls of the vertebral body to form a cavity within the vertebral body. The cavity is then at least partially filled with a material, such as, for example, bone cement.

The balloons may be inserted into the vertebral body using a cannula, for example. Some cannulas include a scoop at the end of the cannula. The balloon engages the scoop to direct inflation of the balloon so that the balloon inflates away from the scoop. However, conventional scoop cannulas fail to prevent the balloon from rolling over the scoop, which causes the balloon to inflate in a direction that was not intended. Furthermore, plastic deformation of the scoop cannula can occur when balloons are inflated to high pressures. Such deformation causes the scoop to bend permanently, which may cause complications when removing the scoop cannula from a vertebral body, for example. This disclosure describes improvements over these prior art technologies.

SUMMARY

In one embodiment, a kyphoplasty cannula comprises a shaft extending between opposite first and second end surfaces. The shaft comprises an inner surface defining a lumen. The shaft comprises a first opening that extends through the first end surface and a second opening that extends through the second end surface. A scoop extends from the second end surface. The scoop comprises an arcuate surface that is continuous with the inner surface. In some embodiments, kits and methods of use are disclosed.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of a surgical system, kit and related methods are discussed in terms of medical devices for performing kyphoplasty. In some embodiments, the system includes a scoop cannula configured to preferentially direct/inflate an inflatable bone tamp. The inflatable bone tamp is positioned within the scoop cannula such that the scoop of the scoop cannula is positioned under a balloon of the inflatable bone tamp to provide a backstop for the balloon to inflate against. The scoop is configured to direct the balloon to a specific area of a patient's anatomy, such as, for example, a vertebral body. For example, in some embodiments, the scoop may be configured to position the balloon adjacent to an end plate or a soft region of bone.

In some embodiments, the scoop cannula comprises a shape memory material. In some embodiments, the scoop cannula comprises a superelastic material. In some embodiments, the scoop cannula comprises super-elastic Nitinol. In some embodiments, the scoop cannula comprises any material that will deform elastically and then return to its original shape to minimize the effects of deformation.

In some embodiments, the scoop cannula comprises a scoop having wings. The wings are configured to support the balloon on the sides as well as the bottom, to prevent the balloon from rolling over the edge of the scoop. This will help distribute the load against the bone, increasing the lifting force.

In some embodiments, one or all of the components of the surgical system may be disposable, peel-pack, pre-packed sterile devices. In some embodiments, the components of the surgical system are configured for one time use and are disposed after they are used one time. However, it is contemplated that one or all of the components of the surgical system may be reusable. The surgical system may be configured as a kit with multiple sized and configured components, including, for example, various scoop cannulas, balloons, etc. In some embodiments, one or more of the components of the surgical system are configured to be sterilized.

In some embodiments, the disclosed surgical system, kits and methods may be alternatively employed in a surgical treatment with a patient in a prone or supine position, and/or employ various surgical approaches, including anterior, posterior, posterior mid-line, direct lateral, postero-lateral, antero-lateral approaches, etc. in any body region. The system, kits and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-14, there are illustrated components of a surgical system 20 in accordance with the principles of the present disclosure.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Surgical system 20 includes a scoop cannula, such as, for example, kyphoplasty cannula 22. Cannula 22 includes a shaft 24 that extends along a longitudinal axis L between a first end surface 26 and an opposite second end surface 28. Shaft 24 comprises an inner surface 30 defining a lumen 32. Lumen 32 is coaxial with axis L and extends the entire length of shaft 24. Lumen 32 has a circular cross-sectional configuration and a uniform diameter along the entire length of lumen 32. In some embodiments, lumen 32 may have various cross section configurations, such as, for example, oval, oblong, triangular, rectangular, square, polygonal, irregular, uniform, non-uniform, variable, tubular and/or tapered. In some embodiments, lumen 32 may be disposed at alternate orientations, relative to axis L, such as, for example, transverse and/or other angular orientations such as acute or obtuse, co-axial and/or may be offset or staggered. Shaft 24 comprises a first opening 34 that extends through end surface 26 and a second opening 36 that extends through end surface 28. Openings 34, 36 are each in communication with lumen 32.

Figure 1:
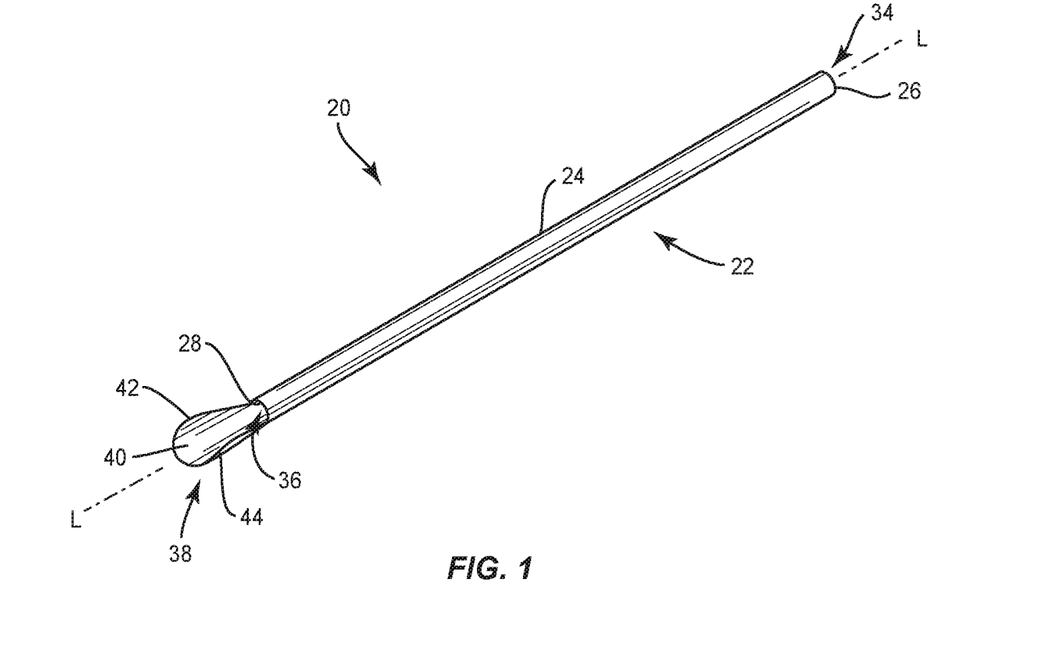
FIG. 1 is a perspective view of a component of a surgical system, in accordance with the present principles of the present disclosure.
Figure 2:
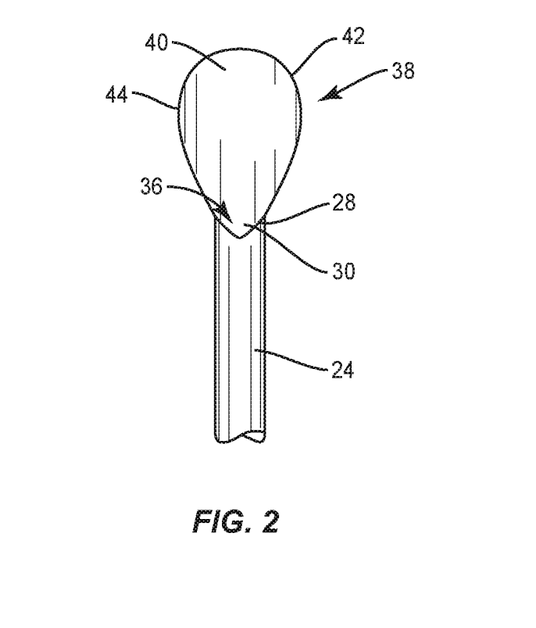
FIG. 2 is an enlarged top view of one end of the component shown in FIG. 1.
Figure 3:
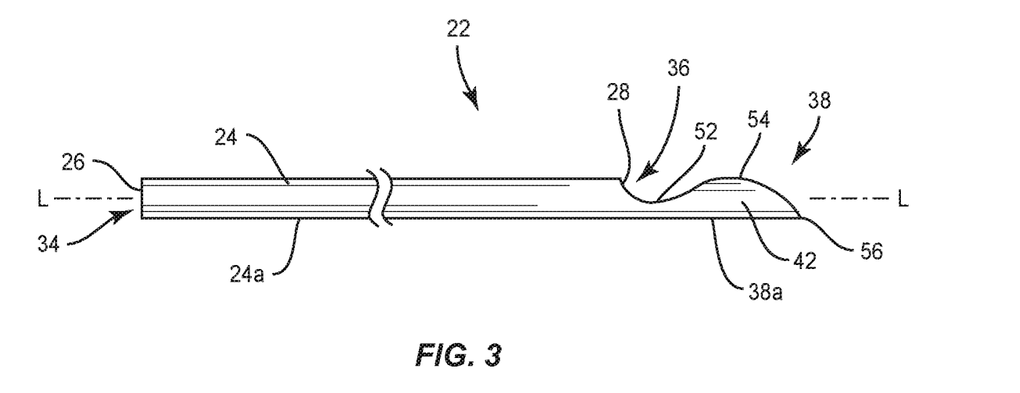
FIG. 3 is a side view of the component shown in FIG. 1.

Cannula 22 includes a scoop 38 extending from end surface 28 along axis L such that scoop 38 faces away from end surface 26. Scoop 38 includes an outer surface 38a that is continuous with an outer surface 24a of shaft 24, as best shown in FIG. 3. That is, there are no gaps or recesses between outer surface 24a and outer surface 38a such that outer surface 24a smoothly transitions into outer surface 38a. In some embodiments, outer surface 38a extends parallel to outer surface 24a and/or axis L along an entire length of scoop 38. In some embodiments, outer surface 38a may be disposed at alternate orientations, relative to outer surface 24a and/or axis L, such as, for example, transverse, perpendicular and/or other angular orientations such as acute or obtuse, co-axial and/or may be offset or staggered.

Scoop 38 includes an arcuate surface 40 that is continuous with inner surface 30 of shaft 24. That is, there are no gaps or recesses between inner surface 30 and arcuate surface 40 such that inner surface 30 smoothly transitions into arcuate surface 40. Arcuate surface 40 is configured to support a bottom surface of a balloon as the balloon is inflated to provide a backstop for the balloon to inflate against, as discussed herein. In some embodiments, arcuate surface 40 is concavely curved from a first side 40a of arcuate surface 40 to a second side 40b of arcuate surface. In some embodiments, arcuate surface 40 is continuously curved from first side 40a of arcuate surface 40 to second side 40b of arcuate surface. In some embodiments, arcuate surface 40 has a continuous radius of curvature from first side 40a of arcuate surface 40 to second side 40b of arcuate surface. In some embodiments, arcuate surface 40 has a radius of curvature from first side 40a of arcuate surface 40 to second side 40b of arcuate surface that is greater than the radius of curvature of inner surface 30 of shaft 24.

Scoop 38 includes a first wing 42 extending outwardly from first side 40a of arcuate surface 40 and a second wing 44 extending outwardly from second side 40b of arcuate surface 40. Wings 42, 44 are each configured to support a side surface of a balloon as the balloon is inflated to prevent the balloon from rolling over scoop 38 as the balloon is inflated, as discussed herein. Wings 42, 44 are each deflectable relative to arcuate surface 40. For example, wings 42, 44 may deflect relative to arcuate surface 40 as the balloon is inflated. In some embodiments, shaft 24 and/or scoop 38 are made from a shape memory material. In some embodiments, shaft 24 and/or scoop 38 are made from a superelastic material. In some embodiments, shaft 24 and/or scoop 38 are made from super-elastic Nitinol. In some embodiments, shaft 24 and/or scoop 38 are made from a material that will deform elastically and then return to its original shape to minimize the effects of deformation. For example, shaft 24 and/or scoop 38 are made from super-elastic Nitinol such that wings 42, 44 will deflect relative to arcuate surface 40 when the balloon is inflated and then return to their original shape after the balloon is deflated.

Figure 4:
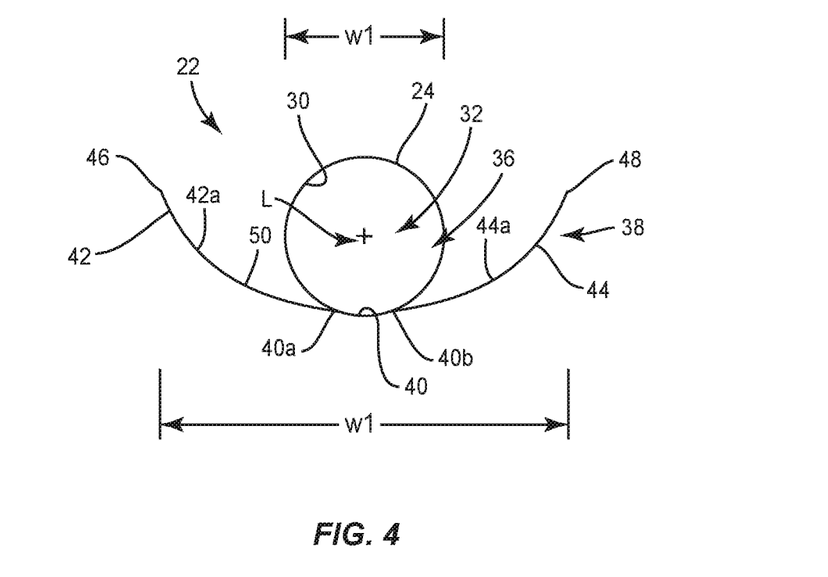
FIG. 4 is an end view of the component shown in FIG. 1.
Figure 5:
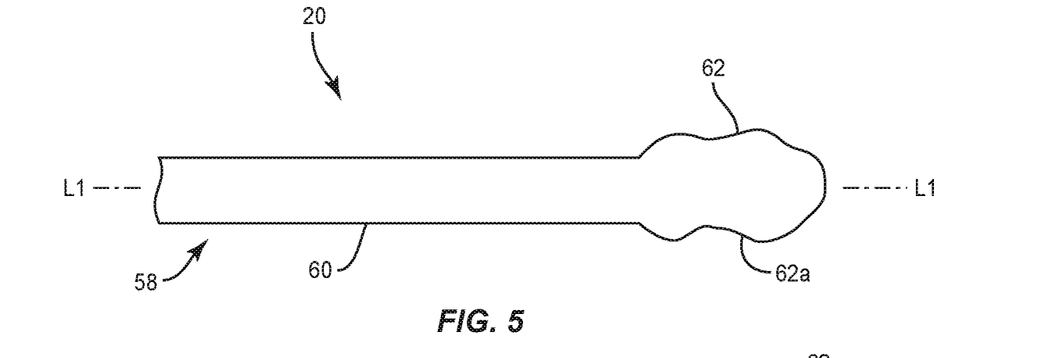
FIG. 5 is a side, cross sectional view of a component of the surgical system, in accordance with the present principles of the present disclosure.

Wing 42 has an inner surface 42a that is continuous with arcuate surface 40 and wing 44 has an inner surface 44a that is continuous with arcuate surface 40, as best shown in FIG. 4. Surface 42a is concavely curved from an end surface 46 of wing 42 to end 40a of arcuate surface 40 and surface 44a is concavely curved from an end surface 48 of wing 44 to end 40b of arcuate surface 40. In some embodiments, surface 42a is continuously curved from an end surface 46 of wing 42 to end 40a of arcuate surface 40 and surface 44a is continuously curved from an end surface 48 of wing 44 to end 40b of arcuate surface 40. In some embodiments, surface 42a has a continuous radius of curvature from an end surface 46 of wing 42 to end 40a of arcuate surface 40 and surface 44a has a continuous radius of curvature from an end surface 48 of wing 44 to end 40b of arcuate surface 40. In some embodiments, surfaces 42a, 44a each have a radius of curvature that is equal to the radius of curvature of arcuate surface 40. In some embodiments, surfaces 42a, 44a each have a radius of curvature that is less than the radius of curvature of arcuate surface 40.

Surfaces 40, 42a, 44a define a concave surface 50 that extends continuously from end surface 46 to end surface 48. In some embodiments, surface 50 is continuously curved from end surface 46 to end surface 48. In some embodiments, surface 50 has a continuous radius of curvature from end surface 46 to end surface 48. In some embodiments, surface 50 has a radius of curvature that is greater than the radius of curvature of inner surface 30 of shaft 24. In some embodiments, the radius of curvature of surface 50 is at least about 2× greater than the radius of curvature of inner surface 30 of shaft 24. In some embodiments, the radius of curvature of surface 50 is at least about 5× greater than the radius of curvature of inner surface 30 of shaft 24. In some embodiments, the radius of curvature of surface 50 is at least about 10× greater than the radius of curvature of inner surface 30 of shaft 24.

Scoop 38 has a width w1 that is defined by the distance from end surface 46 to end surface 48 and shaft 24 has a width w2, as shown in FIG. 4. Width w1 is greater than width w2. In some embodiments, width w1 is about 1.5× greater than width w2. In some embodiments, width w1 is about 2× greater than width w2. In some embodiments, width w1 is about 2.5× greater than width w2. In some embodiments, width w1 is about 3× greater than width w2. In some embodiments, width w1 is about 3.5× greater than width w2. In some embodiments, width w1 is about 4× greater than width w2.

In some embodiments, wings 42, 44 each have an undulating configuration, as shown in FIG. 3. For example, end surfaces 46, 48 may each include a concave portion 52 that extends from end surface 28 of shaft 24 and a convex portion 54 between concave portion 52 and a tip 56 of scoop 38. Concave portion 52 is continuously with end surface 28 and convex portion 54 is continuous with concave portion 54.

Figure 6:
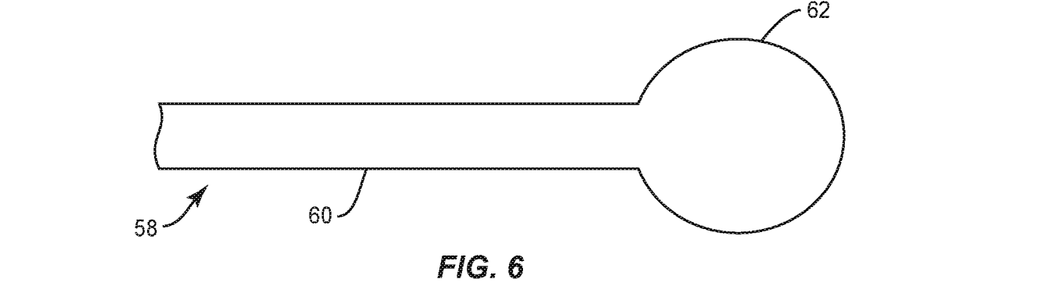
FIG. 6 is a side, cross sectional view of the component shown in FIG. 5.
Figure 7:
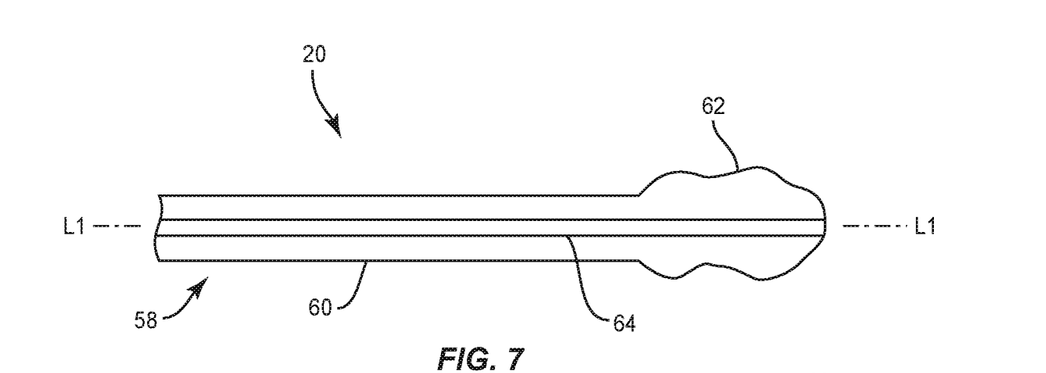
FIG. 7 is a side, cross sectional view of a component of the surgical system, in accordance with the present principles of the present disclosure.
Figure 8:
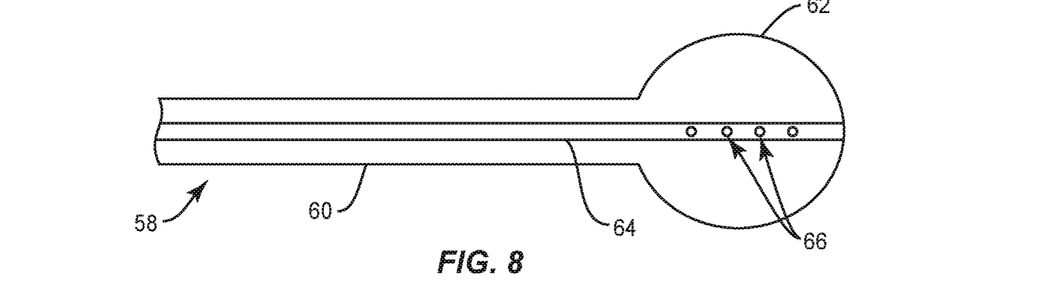
FIG. 8 is a side, cross sectional view of the component shown in FIG. 7.

System 20 includes a balloon catheter, such as, for example, an inflatable bone tamp 58. In one embodiment, shown in FIGS. 5 and 6, inflatable bone tamp 58 includes an outer tube, such as, for example, a tube 60 and a balloon 62 that is coupled to an end of tube 60. An inflation material, such as, for example, air, saline, or a contrast solution may be delivered through tube 60 and into balloon 62 to move balloon 62 from an uninflated orientation shown in FIG. 5 to an inflated orientation shown in FIG. 6. In one embodiment, shown in FIGS. 7 and 8, inflatable bone tamp 58 includes an inner tube, such as, for example a tube 64 positioned within tube 60. A first end of balloon 62 is coupled to an end of tube 60. In some embodiments, an inflation material, such as, for example, air, saline, or a contrast solution may be delivered through the space between tube 60 and tube 64 and into balloon 62 to move balloon 62 from an uninflated orientation shown in FIG. 7 to an inflated orientation shown in FIG. 8. In some embodiments, tube 64 includes one or a plurality of apertures 66 such that an inflation material, such as, for example, air, saline, or a contrast solution may be delivered through tube 64 and into balloon 62 through apertures 66 to move balloon 62 from an uninflated orientation shown in FIG. 7 to an inflated orientation shown in FIG. 8. In some embodiments, balloon 62 is configured to expand radially about a longitudinal axis L1 defined by tube 60, as shown in FIGS. 6 and 8. In some embodiments, balloon 62 may configured to expand in only one direction. For example, balloon 62 may be made such that a top portion of balloon 62 is thicker or comprises a different material than a bottom portion of balloon 62 such that the bottom portion of balloon 62 will expand more than the top portion of balloon 62 when balloon 62 is inflated.

Figure 9:
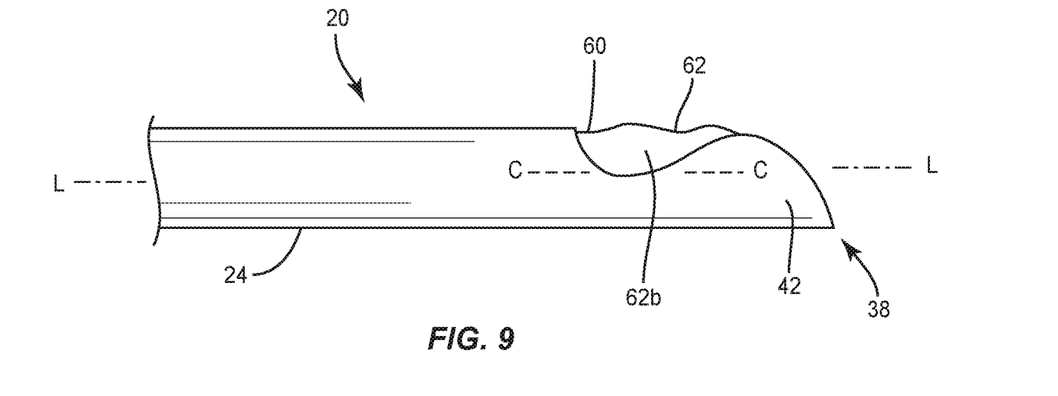
FIG. 9 is a side view of the components shown in FIGS. 1 and 5.
Figure 10:
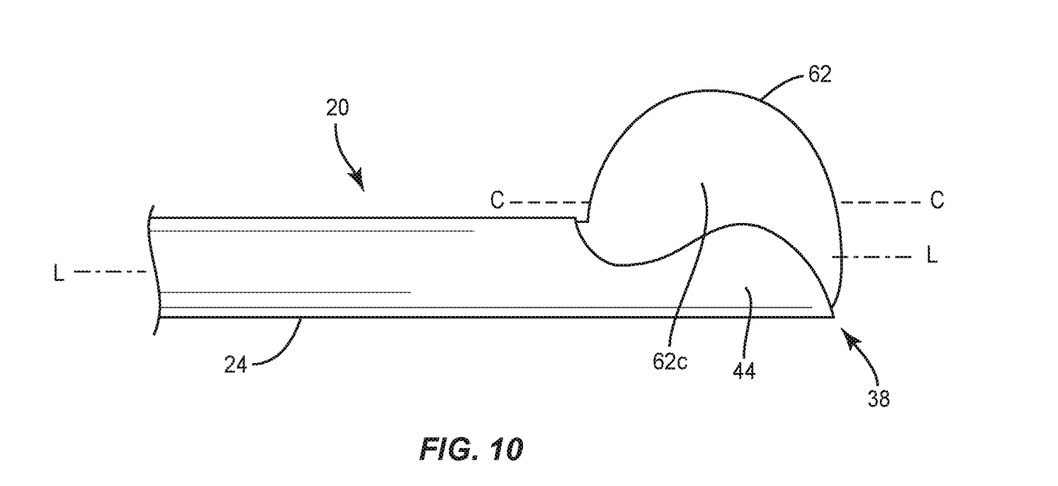
FIG. 10 is a side view of the components shown in FIGS. 1 and 5.

Inflatable bone tamp 58 is configured for insertion into cannula 22 such that tube 60 is positioned within lumen 32 of shaft 24 and balloon 62 is positioned within scoop 38, as shown in FIGS. 9 and 10. In some embodiments, axis L is coaxial with axis L1 when inflatable bone tamp 58 is inserted into cannula 22. When balloon 62 is positioned within scoop 38, a bottom surface 62a of balloon 62 directly engages arcuate surface 40, a first side surface 62b of balloon 62 directly engages inner surface 42a of wing 42 and an opposite second side surface 62c of balloon 62 directly engages inner surface 44a of wing 44. As balloon 62 moves from the uninflated orientation to the inflated orientation, arcuate surface 40 supports bottom surface 62a of balloon 62 as balloon 62 is inflated to provide a backstop for balloon 62 to inflate against such that balloon 62 expands away from arcuate surface 40. Because balloon 62 expands away from scoop 38, a centerline C of balloon 62 is offset from axis L when balloon 62 is inflated, as shown in FIG. 10. In some embodiments, centerline C of balloon 62 may be coaxial with axis L when balloon 62 is uninflated, as shown in FIG. 9. Wing 42 supports side surface 62b of balloon 62 and wing 44 supports side surface 62c of balloon as balloon 62 moves from the uninflated orientation to the inflated orientation to prevent balloon 62 from rolling over scoop 38 as balloon 62 is inflated.

In operation and use, to treat a bone disorder, such as, for example, a spinal fracture, a medical practitioner obtains access to a target location including at least one bony structure, such as, for example, a fractured vertebra V, in any appropriate manner, such as through incision and retraction of tissue. It is envisioned that the surgical system 20 may be used in any existing surgical method or technique including open surgery, mini-open surgery, minimally invasive surgery including percutaneous surgical implantation, whereby vertebra V is accessed through a micro-incision, or sleeve that provides a protected passageway to the area. Once access to the surgical site(s) are obtained, the particular surgical procedure is performed for treating the bone disorder.

Figure 11:
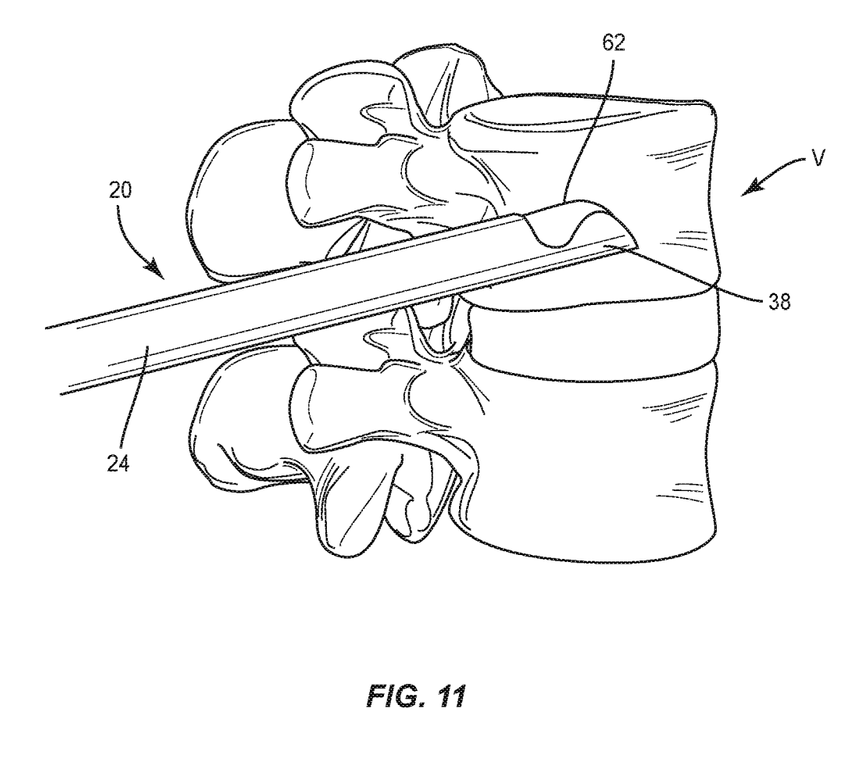
FIG. 11 is a plan view of the components shown in FIGS. 1 and 5.
Figure 12:
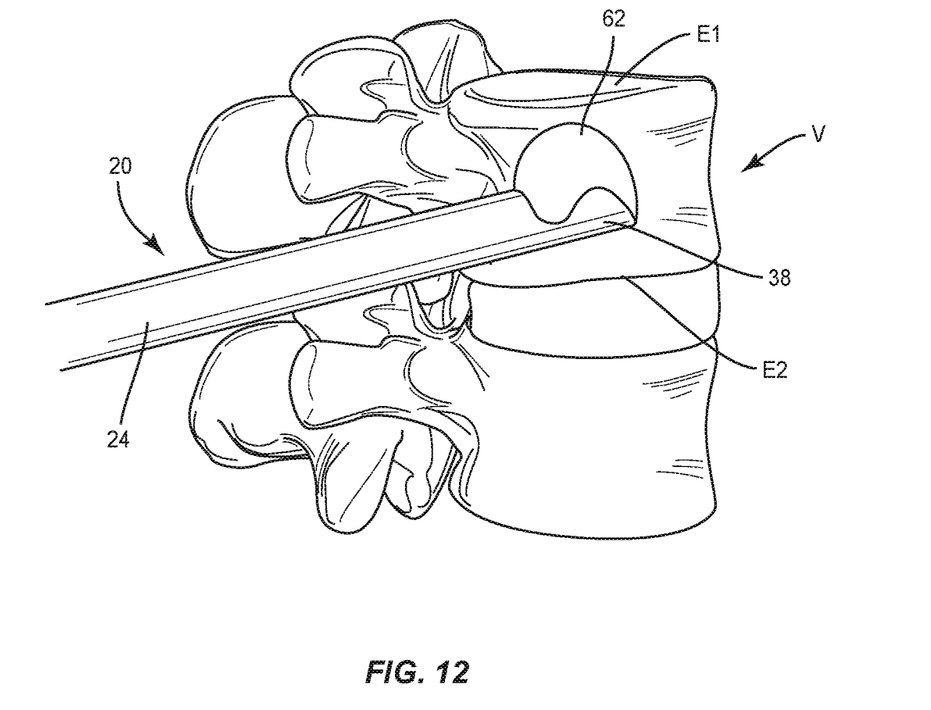
FIG. 12 is a plan view of the components shown in FIGS. 1 and 5.
Figure 13:
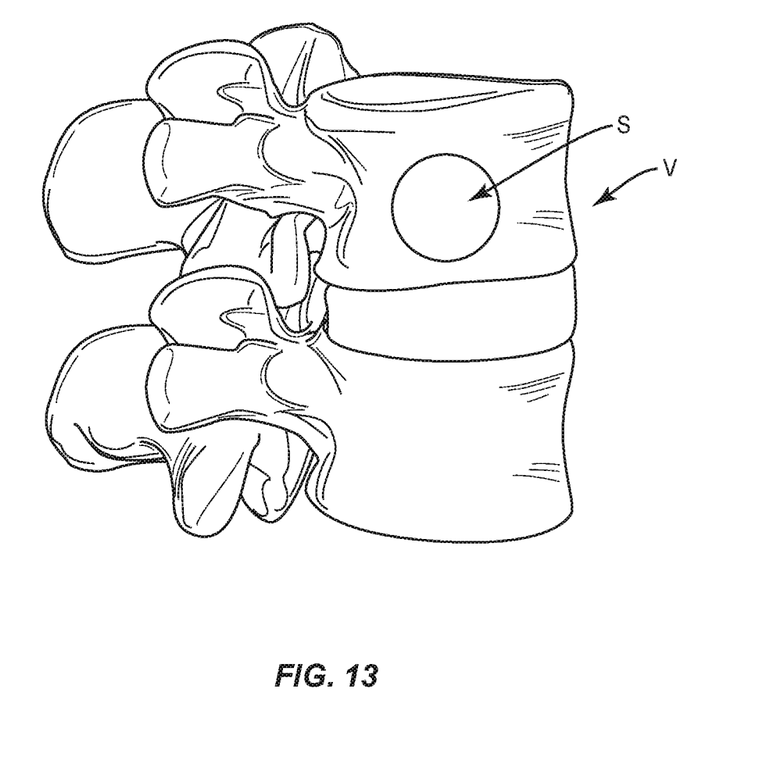
FIG. 13 is a plan view of a surgical site.

Inflatable bone tamp 58 is inserted into cannula 22 such that tube 60 is positioned within lumen 32 of shaft 24 and balloon 62 is positioned within scoop 38. Scoop 38 and balloon 62 are inserted into a vertebral body of vertebra V with balloon 62 in the uninflated orientation, as shown in FIG. 11. Balloon 62 is then moved from the uninflated orientation to the inflated orientation, as shown in FIG. 12. As balloon 62 moves from the uninflated orientation to the inflated orientation, arcuate surface 40 supports bottom surface 62a of balloon 62 as balloon 62 is inflated to provide a backstop for balloon 62 to inflate against such that balloon 62 expands away from arcuate surface 40. This allows a medical practitioner to direct balloon 62 to a selected portion of vertebra V. For example, scoop 38 may be used to direct balloon 62 toward a wall of an endplate E1 of vertebra V, as shown in FIG. 12. That is, rather than allow balloon 62 to expand radially about axis L, scoop 38 causes balloon 62 to expand more toward endplate E1 than toward an endplate E2 of vertebra V. As discussed herein, scoop 38 helps to distribute the load created by balloon 62 against vertebra V to increase the lifting force of balloon 62. As balloon 62 moves from the uninflated orientation to the inflated orientation, wings 42, 44 deflect relative to arcuate surface 40 of scoop 38, as discussed herein. As balloon 62 moves from the uninflated orientation to the inflated orientation, balloon 62 creates a void space S within vertebra V. Balloon 62 is moved from the inflated orientation to the uninflated orientation and cannula 22 is removed from vertebra V, leaving void space S, as shown in FIG. 13. As balloon 62 moves from the inflated orientation to the uninflated orientation, wings 42, 44 returns to their original shape, as discussed herein.

Figure 14:
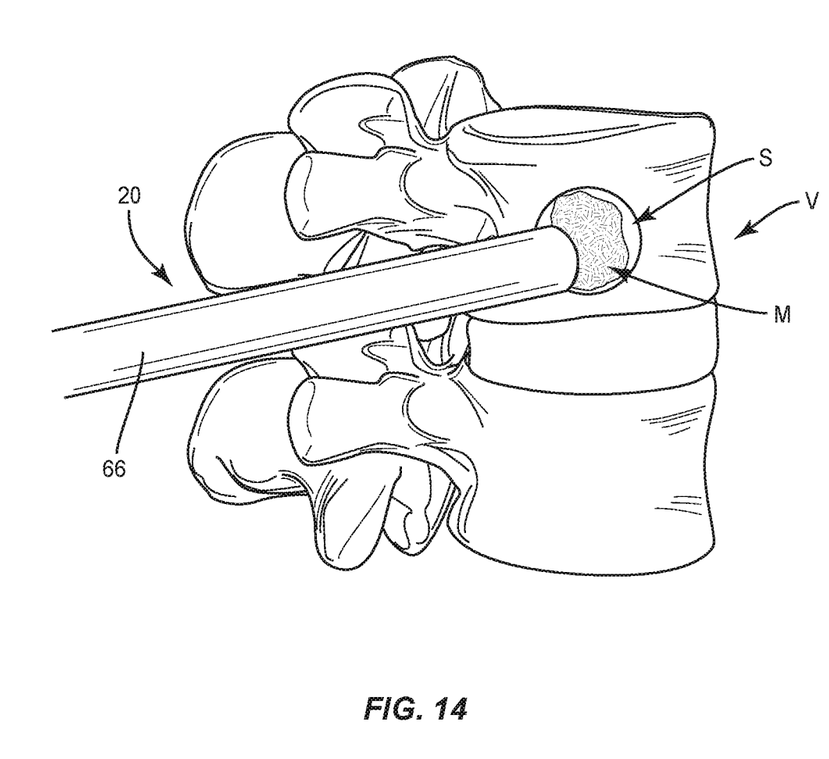
FIG. 14 is a plan view of a component of the surgical system, in accordance with the present principles of the present disclosure.

System 20 includes a second cannula 66 that is inserted into vertebra V such that an end of the cannula is positioned within void space S, as shown in FIG. 14. A material M may be delivered through cannula 66 and into void space S to fill all or a portion of void space S with material M. In some embodiments, material M is a curable bone filler material, such as, for example, bone cement. Material M then cures within vertebra V to treat the fracture by reducing pain from the fracture, stabilizing vertebra V and/or restoring vertebra V back to its normal height.

In some embodiments, a kit containing one or more components of surgical system 20 is provided. The kit may comprise components from any of the embodiments discussed herein. In some embodiments, the kit comprises one or more of the inflation materials discussed herein. In some embodiments, the kit comprises one or more bone filler materials, such as, for example, material M. In some embodiments, the kit comprises a plurality of cannulas, such as, for example, cannulas 22 and/or cannulas 66 having different lengths configured for use with different size patients. In some embodiments, the kit comprises a plurality of cannulas, such as, for example, cannulas 22 having scoops 38 with different widths and/or lengths configured for use with different size balloons.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A kyphoplasty cannula comprising:
   a shaft extending between opposite first and second end surfaces, the shaft comprising an inner surface defining a lumen, the shaft comprising a first opening that extends through the first end surface and a second opening that extends through the second end surface;
   a scoop comprising a proximal end surface coupled directly to the second end surface and an opposite distal end surface, the scoop comprising an arcuate surface that is continuous with the inner surface, the scoop further comprising a first wing and a second wing, the arcuate surface being positioned between the wings, the wings each having an undulating configuration from the proximal end surface to the distal end surface; and
   a balloon catheter comprising an outer tube having opposite proximal and distal end surfaces, the balloon catheter comprising an inner tube positioned within the outer tube, the balloon catheter comprising a balloon having a first end coupled directly to the distal end surface of the outer tube and an opposite second end coupled directly to the inner tube, the balloon being configured to be positioned within the scoop such that a portion of the balloon is capable of extending distal to the distal end surface of the scoop.

2. A kyphoplasty cannula as recited in claim 1, wherein the scoop has a maximum width that is greater than a maximum width of the shaft.

3. A kyphoplasty cannula as recited in claim 1, wherein the arcuate surface is a concave surface.

4. A kyphoplasty cannula as recited in claim 1, wherein the arcuate surface is a concave surface having a continuous radius of curvature.

5. A kyphoplasty cannula as recited in claim 1, wherein the arcuate surface has a radius of curvature that is less than a radius of curvature of the inner surface.

6. A kyphoplasty cannula as recited in claim 1, wherein the undulating configuration comprises a concave portion and a convex portion.

7. A kyphoplasty cannula as recited in claim 1, wherein the wings are deflectable relative to the arcuate surface.

8. A kyphoplasty cannula as recited in claim 1, wherein the shaft and the scoop comprise super-elastic Nitinol.

9. A kyphoplasty kit comprising:
the kyphoplasty cannula recited in claim 1; and
the balloon catheter recited in claim 1.

10. A kyphoplasty cannula as recited in claim 1, wherein:
the inner tube comprises opposite proximal and distal end surfaces;
the second end is coupled directly to the distal end surface of the inner tube; and
the second end is is spaced apart from the outer tube.

11. A kyphoplasty cannula as recited in claim 10, wherein the distal end surface of the inner tube is distal to the distal end surface of the outer tube.

12. A kyphoplasty cannula as recited in claim 11, wherein a center of the balloon is offset from a center of the lumen.

13. A kyphoplasty cannula as recited in claim 1, further comprising a second cannula and bone filler material.

14. A kyphoplasty kit as recited in claim 13, wherein bone filler material is a curable material.

15. A kyphoplasty method comprising:
providing the kyphoplasty cannula recited in claim 1;
inserting the balloon catheter within the lumen such that the balloon directly engages the scoop;
inserting the kyphoplasty cannula through a bony structure such that the balloon is positioned within the bony structure; and
inflating the balloon within the bony structure to create a void within the bony structure.

16. A kyphoplasty method as recited in claim 15, wherein the balloon comprises a bottom surface positioned between opposite first and second side surfaces, the scoop supporting the bottom surface and the side surfaces as the balloon is inflated.

17. A kyphoplasty method as recited in claim 15, wherein the scoop supports the balloon as the balloon is inflated such that the balloon expands away from the scoop as the balloon is inflated.

18. A kyphoplasty method as recited in claim 15, wherein the shaft and the scoop comprise super-elastic Nitinol such that the cannula deforms elastically as the balloon is inflated and then returns to its original shape after the balloon is inflated.

19. A kyphoplasty method as recited in claim 15, further comprising:
uninflating the balloon;
removing the kyphoplasty cannula from the bony structure;
inserting a second cannula into the bony structure such that an end of the second cannula is positioned within the void; and
delivering a bone filler material through the second cannula and into the void; and
allowing the bone filler material to cure within the void.

20. A kyphoplasty cannula as recited in claim 1, wherein the scoop is integrally formed with the shaft.

* * * * *